United States Patent
Han et al.

(10) Patent No.: US 10,401,257 B2
(45) Date of Patent: Sep. 3, 2019

(54) DEVICE AND METHOD FOR TESTING FLOW FIELD STATE WITHIN HIGH-SPEED TRAIN BOGIE CABIN

(71) Applicant: CRRC QINGDAO SIFANG CO., LTD., Qingdao, Shandong (CN)

(72) Inventors: Yundong Han, Shandong (CN); Dawei Chen, Shandong (CN); Peng Lin, Shandong (CN); Shanqiang Fu, Shandong (CN); Weibin Wang, Shandong (CN); Xiaojun Deng, Shandong (CN); Hongju Cui, Shandong (CN); Shaoqing Liu, Shandong (CN); Zhiqiang Zhang, Shandong (CN)

(73) Assignee: CRRC QINGDAO SIFANG CO., LTD., Qingdao, Shandong (CN)

( * ) Notice: Subject to any disclaimer, the term of this patent is extended or adjusted under 35 U.S.C. 154(b) by 211 days.

(21) Appl. No.: 15/504,626

(22) PCT Filed: Sep. 22, 2015

(86) PCT No.: PCT/CN2015/090248
§ 371 (c)(1),
(2) Date: Feb. 16, 2017

(87) PCT Pub. No.: WO2016/050151
PCT Pub. Date: Apr. 7, 2016

(65) Prior Publication Data
US 2017/0234763 A1   Aug. 17, 2017

(30) Foreign Application Priority Data
Sep. 30, 2014   (CN) .......................... 2014 1 0521241

(51) Int. Cl.
| | | |
|---|---|---|
| *G01M 9/00* | (2006.01) | |
| *G01M 17/10* | (2006.01) | |
| *G01N 21/64* | (2006.01) | |
| *G01M 9/06* | (2006.01) | |

(52) U.S. Cl.
CPC .............. *G01M 9/00* (2013.01); *G01M 9/067* (2013.01); *G01M 17/10* (2013.01); *G01N 21/6456* (2013.01)

(58) Field of Classification Search
CPC combination set(s) only.
See application file for complete search history.

(56) References Cited

U.S. PATENT DOCUMENTS 1,676,984 A * 7/1928 Fales et al. ............. G01M 9/04
                                                                73/147
4,896,532 A * 1/1990 Schmalz ............... G01M 9/067
                                                              250/356.1
(Continued)

FOREIGN PATENT DOCUMENTS

CN       1900671 A        1/2007
CN   101424586 A *     5/2009 .............. G01M 9/00
(Continued)

OTHER PUBLICATIONS

International Search Report for PCT/CN2015/090248, dated Dec. 2, 2015, ISA/CN.

*Primary Examiner* — Freddie Kirkland, III
(74) *Attorney, Agent, or Firm* — Yue (Robert) Xu; Apex Attorneys at Law, LLP

(57) ABSTRACT

A device for testing a flow field state within a high-speed train bogie cabin; the periphery of a bogie consists of apron plates and end plates; the test device comprises: a plurality of test points evenly distributed on the inner walls of the apron plates and end plates, a plurality of image pickup devices installed in the bogie cabin, a smoke generator communicating with an inner cavity of the bogie via pipes, (Continued)

and one or more smoke exits provided on top of the bogie; each test point is connected to a test tape, and the distance between the test points is more than twice the test tape length. The test device monitors and records in real time the air flow direction at the end plates and apron plates by means of viewing of a fluorescent test tape. Also provided is a method of testing a flow field state within a high-speed train bogie cabin.

15 Claims, 2 Drawing Sheets

(56) References Cited

U.S. PATENT DOCUMENTS

| | | | | |
|---|---|---|---|---|
| 5,127,264 A * | 7/1992 | Schmalz | ............... | G01M 9/067 |
| | | | | 73/147 |
| 5,647,054 A * | 7/1997 | Jones | ..................... | F41H 9/06 |
| | | | | 165/155 |
| 9,057,709 B2 * | 6/2015 | Li | ............................ | G01P 5/10 |
| 9,182,422 B2 * | 11/2015 | Hoshishima | .......... | G01M 9/067 |

FOREIGN PATENT DOCUMENTS

| | | | | |
|---|---|---|---|---|
| CN | 101424586 A | | 5/2009 | |
| CN | 101509826 A | | 8/2009 | |
| CN | 202329982 U | * | 7/2012 | ............. G01M 9/00 |
| CN | 202329982 U | | 7/2012 | |
| CN | 104266815 A | | 1/2015 | |
| CN | 204116011 U | | 1/2015 | |
| JP | 2001133358 A | | 5/2001 | |
| KR | 20090076175 A | | 7/2009 | |

\* cited by examiner

DEVICE AND METHOD FOR TESTING FLOW FIELD STATE WITHIN HIGH-SPEED TRAIN BOGIE CABIN

This application is a National Phase entry of PCT Application No. PCT/CN2015/090248, filed Sep. 22, 2015, which claims the benefit of priority to Chinese Patent Application No. 201410521241.0, titled "DEVICE AND METHOD FOR TESTING FLOW FIELD STATE WITHIN HIGH-SPEED TRAIN BOGIE CABIN", filed with the Chinese State Intellectual Property Office on Sep. 30, 2014, the entire disclosures of which are incorporated herein by reference.

TECHNICAL FIELD

The present application relates to the field of railway vehicle technology, and in particular to a device and a method for testing a flow field state within a bogie cabin of a high-speed train.

BACKGROUND

Snow accumulating and icing may occur in a bogie in the case that a high-speed train runs in the wind and snow. In order to solve the problem of the snow accumulating and icing in the bogie, it is required to know a flow condition of air within a bogie cabin. A flow direction of air at an end plate at each side and an apron plate at each side of the bogie cabin is vitally important for determining an improved solution of preventing snow accumulating. The flow condition of the air in the bogie cabin is very complicated due to a complicated inner structure of the bogie. Although a flow field condition within the bogie cabin can be obtained by using a simulation calculation method, the structure of the bogie may be simplified due to limit of calculation condition in simulation calculation, thus, it is hard to avoid a difference between a computed result and a real flow state of the air in the bogie cabin, which may have a detrimental effect on determining the improved solution of preventing snow accumulating, causing the snow accumulating and icing in the bogie cannot be removed completely.

SUMMARY (1) Technical Issue to be Addressed

The technical issue to be addressed according to the present application is as follows. In the case that a high-speed train runs in the wind and snow, snow accumulating and icing are easy to occur within a bogie cabin, thus, it is required to improve a solution based on a flow state of airflow in the bogie so as to reduce the occurrence of snow accumulating and icing. Although a simulated condition of the airflow can be obtained by simulation calculation, it is required to simplify a model of the bogie to perform the simulation calculation due to a complicated inner structure of the bogie and limit of a calculation condition. There is inevitably a difference between the obtained result and a real flow state of the airflow in the bogie cabin, which has a serious effect on determining an improved solution of preventing snow accumulating, and then the snow accumulating and icing cannot be prevented completely.

(2) Technical Solutions

To solve the above-described technical issue, a device for testing a flow field state within a bogie cabin of a high-speed train is provided according to the present application, which includes: multiple test points evenly arranged on inner walls of an apron plate and an end plate on the periphery of a bogie, multiple image pick-up devices installed in the bogie cabin, a smoke generator in communication with an inner cavity of the bogie via a pipe, and one or more smoke exits arranged on top of the bogie, each of the test points is in connection with a test strip, and the distance between any two adjacent test points is greater than twice of the length of the test strip. The smoke generator is provided for spraying smoke into the bogie cabin, and a camera is provided for capturing a deflection state of the test strip and a motion state of the smoke.

The test strip is in a soft stripe-shaped structure, which has one end fixed at the test point and another end hanging freely and swinging with motion of airflow.

The test strip is coated with a fluorescent layer.

The image pick-up devices are provided with a light compensation unit for enabling the image pick-up device to obtain a clear image or video.

The smoke generator is arranged outside the bogie cabin and is in communication with the bogie cabin via a pipe.

The smoke sprayed by the smoke generator is colorful smoke.

A method for testing a flow field state within a bogie cabin of a high-speed train includes:

S1: turning on image pick-up devices in a running state of the train to shoot a deflection direction of a test strip at each of test points on inner walls of an apron plate and an end plate;

S2: analyzing a motion state of airflow at the test points based on a shooting result of step S1;

S3: turning on a smoke generator and image pick-up devices, smoke sprayed by the smoke generator enters into the bogie cabin through a pipe, and moves with airflow in the bogie cabin, and is finally vented from a smoke exit; and shooting, by the image pick-up devices, the motion state of the smoke in a real time manner; and S4: analyzing based on the motion state of the smoke shot in step S3 to obtain a motion trail of the smoke within the bogie cabin.

The light compensation unit is automatically turned on or turned off based on a lighting condition in the bogie in steps S1 and S3.

Preferably, the step S1 and the step S3 are performed simultaneously.

Preferably, the step S1 and the step S3 are performed independently.

(3) Beneficial Effects

The above-described technical solution has the following advantages:

1) the test method is simple, safe and effective, and can present a real flow state of air within the bogie cabin;

2) the test device has a simple structure, and with which, the test has a low cost, and a good effect, and test point arrangement is simple and easy in operation;

3) a flow direction of air at the end plate at each side and the apron plate at each side of the bogie cabin can be monitored and recorded in a real time manner by observing the fluorescent test strip; and 4) with the colorful smoke sprayed into the bogie cabin by a colorful smoke discharger, and based on a motion trail of the colorful smoke, the airflow condition within a region in the bogie cabin is monitored in a real time manner.

BRIEF DESCRIPTION OF THE DRAWINGS

Technical solutions of the embodiments according to the present application and/or the conventional art will be illustrated more clearly with the following brief description of the drawings. Apparently, the drawings referred in the following description constitute only some embodiments of the application. Those skilled in the art may obtain some other drawings from these drawings without any creative work.

REFERENCE NUMERALS IN THE DRAWINGS

Figure 1:
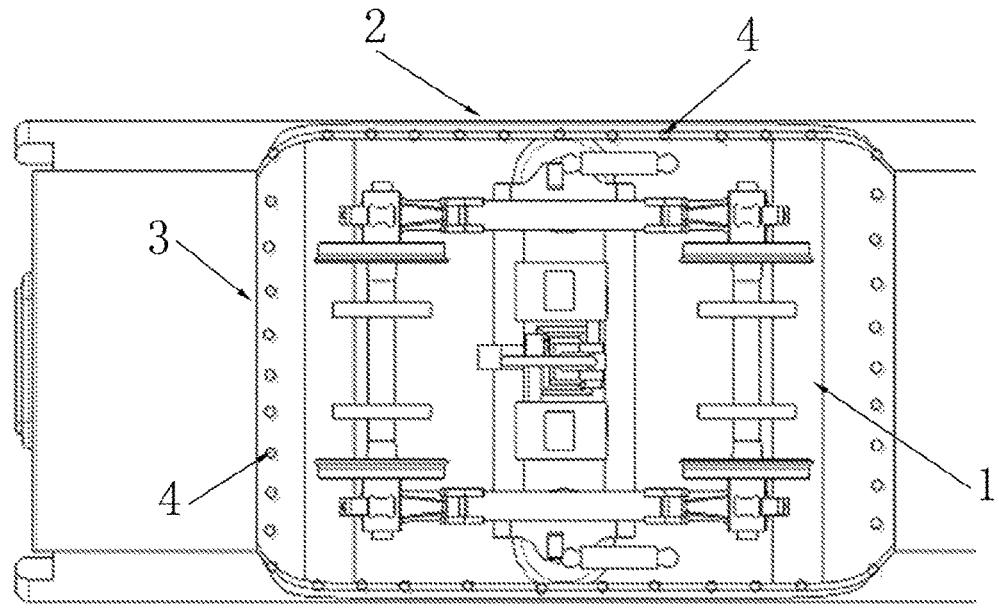
FIG. 1 is a schematic plan view showing the structure of a device for testing a flow filed state within a bogie cabin of a high-speed train according to the present application.
Figure 2:
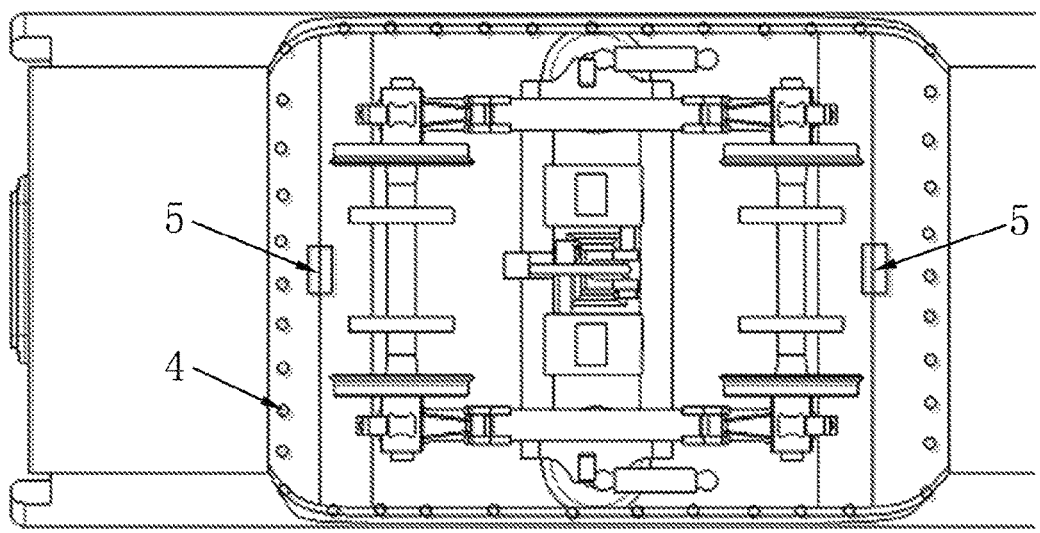
FIG. 2 is a schematic view of distribution of image pick-up devices according to the present application and test points on a bogie.

| 1 | bogie, | 2 | apron plate, | 3 | end plate, |
|---|---|---|---|---|---|
| 4 | test point, | 5 | image pick-up device, | 6 | smoke generator, |
| 7 | smoke exit. | | | | |

DETAILED DESCRIPTION OF EMBODIMENTS

Technical solutions according to embodiments of the present application are described clearly and completely in conjunction with the drawings in the embodiments of the present application hereinafter. Apparently, the described embodiments are only a few rather than all of the embodiments of the present application. Other embodiments obtained by those skilled in the art without any creative work based on the embodiments of the present application fall into the scope of protection of the present application.

As shown in FIGS. 1 to 4, a device and a method for testing a flow field state within a bogie cabin of a high-speed train are provided according to the present application. The device for testing the flow field state within the bogie cabin of the high-speed train is provided for testing the flow field state of air in the bogie cabin, which includes: multiple test strips (not shown) fixed on inside walls of an apron plate 2 and an end plate 3, a image pick-up device 5 arranged in the bogie cabin, a smoke generator 6 arranged outside the bogie cabin and in communication with the bogie cabin via a pipe (not shown), and one or more smoke exits 7 arranged on top of the bogie 1, multiple evenly distributed test points 4 are selected on inner walls of the apron plate 2 and the end plate 3, where each of the test points 4 is connected to one test strip which is made of a soft strip-shaped material, preferably a strip of cloth or silk ribbon. For ease of observation, the test strip may be coated with a fluorescent layer. the test strip has one end fixed at the test point 4 and another end hanging freely and swinging with motion of airflow. To prevent the test strips from winding each other, the distance between any two adjacent test points 4 is set to be greater than twice of the length of the test strip.

The deflection state of the test strip refers to a deflection direction of the test strip under airflow blowing relative to a natural hanging state, which can represent a flow direction of air. The motion state of smoke refers to a motion trail of the smoke during a time period from the smoke entering the bogie cabin to the smoke leaving from the smoke exit, and the motion trail is obtained by processing images or videos shot at different time points.

Figure 3:
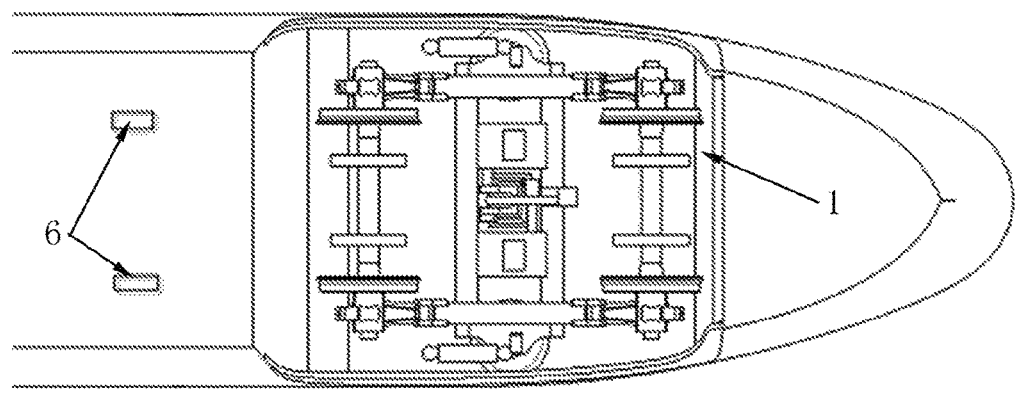
FIG. 3 is a view of positional relationship between a smoke generator according to the present application and a bogie.
Figure 4:
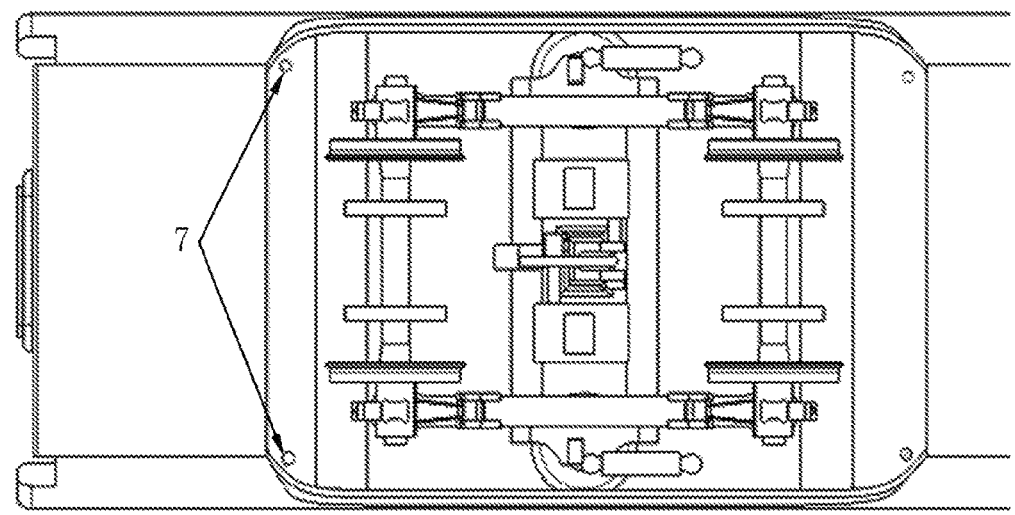
FIG. 4 is a schematic view of distribution of a smoke exit according to the present application on a bogie.

Since the smoke generator 6 is arranged in the bogie cabin and has a large volume, the smoke generator 6 may have a significant effect on motion of airflow in the bogie cabin. Therefore, as shown in FIG. 3, the smoke generator 6 is arranged outside the bogie cabin and in communication with the bogie cabin by the pipe. The smoke generator 6 may spray colorful smoke, and the smoke enters into the bogie cabin through the pipe, and then flows along with air in the cabin, and is finally vented from the smoke exit 7 at top of the bogie 1.

The image pick-up device 5 can rotate freely, and is easy to have its direction adjusted for obtaining clear videos or photos of strip fluttering or smoke flowing and further for analyzing a distribution state of the flow field in the bogie 1. The image pick-up device 5 is provided with a light compensation unit. The light compensation unit is turned on for compensating light for the image pick-up device 5 in the case that light in the bogie cabin is dark and clear photo cannot be obtained. The image pick-up device 5 can be fixed at an appropriate position in accordance with specific conditions for obtaining the best shooting angle.

A method for testing the flow field state within the bogie cabin by using the above-described device is further disclosed according to the present application, which includes the following steps:

S1: turning on the image pick-up device 5 in a running state of the train to shoot a deflection direction of the test strip at each of the test points 4 on the inner walls of the end plate 3 and the apron plate 2, where the deflection direction can represent a whole flow direction of airflow at each of the test points 4, for example, forward or backward;

S2: analyzing a motion state of airflow at each of the test points 4 based on a shot result of step S1, i.e., analyzing based on the deflection direction of the test strip at each of the test points 4 in the photos or videos to obtain a flow direction of air at the inner walls of the end plate 3 and the apron plate 2 of the bogie 1;

S3: turning on the smoke generator 6 and the image pick-up device 5, wherein the sprayed smoke enters into the bogie cabin through the pipe, and moves with airflow in the bogie cabin, and is finally vented from the smoke exit 7; and shooting, by the image pick-up device 5, the motion state of the smoke in a real time manner in the process that the smoke passes through the bogie cabin; and S4: analyzing based on the motion state of the smoke in different time points which are shot in step S3 to obtain a motion trail of the smoke in the bogie cabin, to obtain the flow field state within the bogie cabin.

In consideration of factors such as weather change and a dark night light, in step S1 and step S3, the light compensation unit detects the light intensity in the bogie cabin in a real time manner and is automatically turned on or turned off depending on a lighting condition in the bogie 1 for compensating light for the image pick-up devices 5, so as to obtain the clearest video or photo and improve the accuracy of the test.

Step S1 and step S3 may be performed simultaneously in test, and then a complete flow field state within the bogie cabin can be obtained. Step S1 or step S3 may also be performed independently if necessary, that is, only one of the air flow state and the smoke motion state is to be tested, for example, no smoke is sprayed and only the deflection conditions of the test strips are observed to measure the air flow state on the inner walls of the apron plate 2 and the end plate 3.

As described in the above embodiment, in the present application, the test strips and the image pick-up device 5 are arranged in the bogie cabin, and colorful smoke is passed into the bogie cabin through the pipe, thus a flow process of the air in the bogie cabin can be observed directly. The image pick-up device 5 records the motion states of the test strips and the smoke in a real time manner, thus a real flow field state within the bogie cabin may be obtained. The test is performed in the bogie cabin of the high-speed train in the running state, and all the data are obtained by real-time collecting, thus, there is no need to perform simplification and simulation calculation on the bogie 1, and the real flow field state within the bogie cabin can be obtained by a simple processing to the bogie 1. The test strip may be made of a common material such as cloth or silk ribbon. For ease of observation, the test strip may be coated with a layer of fluorescent powder to form a fluorescent layer, and the operation is simple. The test strip is directly adhered to the inner walls of the bogie 1, thus, the test device has a simple structure and a low production cost. The smoke generator 6 with a relative large volume is arranged outside the bogie cabin, thereby avoiding affecting the flow field in the bogie cabin. The complete test has a simple structure, and the test method is easy to operate. It is only required to turn on the smoke generator 6 and process the shot result, and the flow field state within the bogie cabin can be obtained.

Those described above are only preferable embodiments according to the present application. It should be noted that, for those skilled in the art, improvements and substitutions may also be made without departing from the technical principle of the present application. Those improvements and substitutions should also be deemed as falling in the scope of protection of the present invention.

The invention claimed is:

1. A device for testing a flow field state within a cabin of a bogie of a high-speed train, comprising:
   a plurality of test points evenly arranged on inner walls of an apron plate and an end plate on the periphery of the bogie;
   a plurality of image pick-up devices installed in the cabin;
   a smoke generator in communication with an inner cavity of the bogie via a pipe; and
   one or more smoke exits arranged on top of the bogie, wherein:
   each of the test points is connected to a test strip,
   the distance between any two adjacent test points is greater than twice of a length of the test strip,
   the smoke generator is provided for spraying smoke into the cabin, and
   the plurality of image pick-up devices is provided for capturing a deflection state of the test strip and a motion state of the smoke.

2. The device for testing the flow field state within the cabin of the bogie of the high-speed train according to claim 1, wherein the test strip is in a soft stripe-shaped structure, which has one end fixed at the test point and another end hanging freely and swinging with motion of airflow.

3. The device for testing the flow field state within the cabin of the bogie of the high-speed train according to claim 2, wherein the test strip is coated with a fluorescent layer.

4. A method for testing a flow field state within a cabin of a bogie of a high-speed train by using the device for testing the flow field state within the bogie of the cabin of the high-speed train according to claim 3, comprising:
   S1: turning on the image pick-up devices in a running state of the train to shoot a deflection direction of the test strip at each of the test points on the inner walls of the apron plate and the end plate;
   S2: analyzing a motion state of airflow at the test points based on a shooting result of step S1;
   S3: turning on the smoke generator and the image pick-up devices, wherein smoke sprayed by the smoke generator enters into the cabin through the pipe and moves with airflow in the cabin, and is finally vented from the one or more smoke exits; and shooting, by the image pick-up devices, the motion state of the smoke in a real time manner; and
   S4: analyzing based on the motion state of the smoke shot in step S3 to obtain a motion trail of the smoke within the cabin.

5. A method for testing a flow field state within a cabin of a bogie of a high-speed train by using the device for testing the flow field state within the bogie of the cabin of the high-speed train according to claim 2, comprising:
   S1: turning on the image pick-up devices in a running state of the train to shoot a deflection direction of the test strip at each of the test points on the inner walls of the apron plate and the end plate;
   S2: analyzing a motion state of airflow at the test points based on a shooting result of step S1;
   S3: turning on the smoke generator and the image pick-up devices, wherein smoke sprayed by the smoke generator enters into the cabin through the pipe and moves with airflow in the cabin, and is finally vented from the one or more smoke exits; and shooting, by the image pick-up devices, the motion state of the smoke in a real time manner; and
   S4: analyzing based on the motion state of the smoke shot in step S3 to obtain a motion trail of the smoke within the cabin.

6. The device for testing the flow field state within the cabin of the bogie of the high-speed train according to claim 1, wherein the plurality of image pick-up devices is provided with a light compensation unit for allowing the image pick-up devices to obtain a clear image or video.

7. A method for testing a flow field state within a cabin of a bogie of a high-speed train by using the device for testing the flow field state within the bogie of the cabin of the high-speed train according to claim 6, comprising:
   S1: turning on the image pick-up devices in a running state of the train to shoot a deflection direction of the test strip at each of the test points on the inner walls of the apron plate and the end plate;
   S2: analyzing a motion state of airflow at the test points based on a shooting result of step S1;
   S3: turning on the smoke generator and the image pick-up devices, wherein smoke sprayed by the smoke generator enters into the cabin through the pipe and moves with airflow in the cabin, and is finally vented from the one or more smoke exits; and shooting, by the image pick-up devices, the motion state of the smoke in a real time manner; and
   S4: analyzing based on the motion state of the smoke shot in step S3 to obtain a motion trail of the smoke within the cabin.

8. A method for testing a flow field state within a cabin of a bogie of a high-speed train by using the device for testing the flow field state within the bogie of the cabin of the high-speed train according to claim 6, comprising:
   S1: turning on the image pick-up devices in a running state of the train to shoot a deflection direction of the test strip at each of the test points on the inner walls of the apron plate and the end plate;

S2: analyzing a motion state of airflow at the test points based on a shooting result of step S1;

S3: turning on the smoke generator and the image pick-up devices, wherein smoke sprayed by the smoke generator enters into the cabin through the pipe and moves with airflow in the cabin, and is finally vented from the one or more smoke exits; and shooting, by the image pick-up devices, the motion state of the smoke in a real time manner; and S4: analyzing based on the motion state of the smoke shot in step S3 to obtain a motion trail of the smoke within the cabin.

9. The method for testing the flow field state within the cabin of the bogie of the high-speed train according to claim 8, wherein the light compensation unit is automatically turned on or turned off based on a lighting condition in the bogie in steps S1 and S3.

10. The method for testing the flow field state within the cabin of the bogie of the high-speed train according to claim 8, wherein the step S1 and the step S3 are performed simultaneously.

11. The method for testing the flow field state within the cabin of the bogie of the high-speed train according to claim 8, wherein the step S1 and the step S3 are performed independently.

12. The device for testing the flow field state within the cabin of the bogie of the high-speed train according to claim 1, wherein the smoke generator is arranged outside the cabin and is in communication with the cabin via a pipe.

13. A method for testing a flow field state within a cabin of a bogie of a high-speed train by using the device for testing the flow field state within the bogie of the cabin of the high-speed train according to claim 12, comprising:

S1: turning on the image pick-up devices in a running state of the train to shoot a deflection direction of the test strip at each of the test points on the inner walls of the apron plate and the end plate;

S2: analyzing a motion state of airflow at the test points based on a shooting result of step S1;

S3: turning on the smoke generator and the image pick-up devices, wherein smoke sprayed by the smoke generator enters into the cabin through the pipe and moves with airflow in the cabin, and is finally vented from the one or more smoke exits; and shooting, by the image pick-up devices, the motion state of the smoke in a real time manner; and S4: analyzing based on the motion state of the smoke shot in step S3 to obtain a motion trail of the smoke within the cabin.

14. The device for testing the flow field state within the cabin of the bogie of the high-speed train according to claim 1, wherein the smoke sprayed by the smoke generator is colorful smoke.

15. A method for testing a flow field state within a cabin of a bogie of a high-speed train by using the device for testing the flow field state within the bogie of the cabin of the high-speed train according to claim 14, comprising:

S1: turning on the image pick-up devices in a running state of the train to shoot a deflection direction of the test strip at each of the test points on the inner walls of the apron plate and the end plate;

S2: analyzing a motion state of airflow at the test points based on a shooting result of step S1;

S3: turning on the smoke generator and the image pick-up devices, wherein smoke sprayed by the smoke generator enters into the cabin through the pipe and moves with airflow in the cabin, and is finally vented from the one or more smoke exits; and shooting, by the image pick-up devices, the motion state of the smoke in a real time manner; and S4: analyzing based on the motion state of the smoke shot in step S3 to obtain a motion trail of the smoke within the cabin.

* * * * *